(12) United States Patent
Shehada et al.

(10) Patent No.: US 7,534,207 B2
(45) Date of Patent: May 19, 2009

(54) IMPLANTABLE DEVICE WITH SENSORS FOR DIFFERENTIAL MONITORING OF INTERNAL CONDITION

(75) Inventors: Ramez Emile Necola Shehada, La Mirada, CA (US); Nicolas Jabbour, Pasadena, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 79 days.

(21) Appl. No.: 10/789,492

(22) Filed: Feb. 26, 2004

(65) Prior Publication Data

US 2004/0236192 A1 Nov. 25, 2004

Related U.S. Application Data

(60) Provisional application No. 60/449,963, filed on Feb. 26, 2003, provisional application No. 60/445,714, filed on Feb. 7, 2003, provisional application No. 60/453,009, filed on Mar. 6, 2003.

(51) Int. Cl.
*A61B 5/00* (2006.01)
(52) U.S. Cl. ................... 600/309; 600/301; 600/373
(58) Field of Classification Search ......... 600/309–342, 600/373
See application file for complete search history.

(56) References Cited

U.S. PATENT DOCUMENTS

| | | | |
|---|---|---|---|
| 4,531,526 A | 7/1985 | Genest | |
| 4,703,756 A * | 11/1987 | Gough et al. | 600/347 |
| 5,029,582 A | 7/1991 | Lekholm | |
| 5,106,387 A | 4/1992 | Kittrell et al. | |
| 5,197,470 A * | 3/1993 | Helfer et al. | 600/342 |
| 5,218,962 A * | 6/1993 | Mannheimer et al. | 600/331 |
| 5,622,428 A | 4/1997 | Bonnet | |
| 5,704,352 A | 1/1998 | Tremblay et al. | |
| 5,730,125 A * | 3/1998 | Prutchi et al. | 600/323 |
| 5,769,791 A | 6/1998 | Benaron et al. | |
| 5,785,658 A | 7/1998 | Benaron et al. | |
| 5,797,398 A | 8/1998 | Bowman | |
| 5,916,171 A | 6/1999 | Mayevsky | |
| 5,954,053 A * | 9/1999 | Chance et al. | 600/310 |
| 5,987,346 A * | 11/1999 | Benaron et al. | 600/407 |
| 5,999,848 A * | 12/1999 | Gord et al. | 607/2 |
| 6,106,477 A * | 8/2000 | Miesel et al. | 600/486 |
| 6,122,536 A * | 9/2000 | Sun et al. | 600/341 |
| 6,123,719 A * | 9/2000 | Masychev | 600/407 |
| 6,200,265 B1 | 3/2001 | Walsh et al. | |
| 6,201,980 B1 | 3/2001 | Darrow et al. | |
| 6,215,403 B1 | 4/2001 | Chan et al. | |
| 6,230,059 B1 | 5/2001 | Duffin | |
| 6,358,202 B1 | 3/2002 | Arent | |
| 6,358,203 B2 | 3/2002 | Bardy | |
| 6,364,834 B1 | 4/2002 | Reuss et al. | |
| 6,402,689 B1 | 6/2002 | Scarantino et al. | |

(Continued)

*Primary Examiner*—Patricia Mallar
*Assistant Examiner*—Karen E Toth
(74) *Attorney, Agent, or Firm*—McDermott Will & Emery LLP

(57) ABSTRACT

The present invention is directed to implantable devices and systems for the differential monitoring the condition of the tissue or fluid emitted from the site in proximity to the implants. The invention may also include modifications of the implantable device to stabilize or immobilize the device in the proximity of the tissue to be monitored.

11 Claims, 13 Drawing Sheets

U.S. PATENT DOCUMENTS

| | | | |
|---|---|---|---|
| 6,409,674 B1 | 6/2002 | Brockway et al. | |
| 6,474,341 B1 | 11/2002 | Hunter et al. | |
| 6,485,416 B1 | 11/2002 | Platt et al. | |
| 6,499,488 B1 | 12/2002 | Hunter et al. | |
| 6,572,543 B1 | 6/2003 | Christopherson et al. | |
| 6,582,365 B1 * | 6/2003 | Hines et al. | 600/300 |
| 6,587,701 B1 * | 7/2003 | Stranc et al. | 600/310 |
| 6,591,134 B2 | 7/2003 | Busch et al. | |
| 6,592,518 B2 | 7/2003 | Denker et al. | |
| 6,599,241 B1 | 7/2003 | Murphy | |
| 6,602,191 B2 | 8/2003 | Quy | |
| 6,605,039 B2 | 8/2003 | Houben et al. | |
| 6,616,606 B1 | 9/2003 | Petersen et al. | |
| 6,622,043 B1 | 9/2003 | Kraus et al. | |
| 6,636,769 B2 | 10/2003 | Govari et al. | |
| 6,638,231 B2 | 10/2003 | Govari et al. | |
| 6,645,143 B2 | 11/2003 | VanTassel et al. | |
| 6,650,932 B1 | 11/2003 | Menzie et al. | |
| 6,650,939 B2 | 11/2003 | Taepke et al. | |
| 6,654,629 B2 | 11/2003 | Montegrande | |
| 6,656,117 B2 | 12/2003 | Jentsch et al. | |
| 6,659,948 B2 | 12/2003 | Lebel et al. | |
| 6,662,052 B1 | 12/2003 | Sarwal et al. | |
| 6,673,596 B1 | 1/2004 | Sayler et al. | |
| 6,681,127 B2 | 1/2004 | March | |
| 6,682,480 B1 | 1/2004 | Habib et al. | |
| 6,682,490 B2 | 1/2004 | Roy et al. | |
| 6,685,634 B1 | 2/2004 | Fry | |
| 6,687,546 B2 | 2/2004 | Lebel et al. | |
| 6,711,426 B2 | 3/2004 | Benaron et al. | |
| 2002/0077671 A1 | 6/2002 | Govari et al. | |
| 2002/0077672 A1 | 6/2002 | Govari et al. | |
| 2002/0120200 A1 | 8/2002 | Brockway et al. | |
| 2002/0183629 A1 * | 12/2002 | Fitz | 600/488 |
| 2003/0109772 A1 | 6/2003 | Mills | |
| 2003/0125612 A1 | 7/2003 | Fox et al. | |
| 2003/0136417 A1 | 7/2003 | Fonseca et al. | |
| 2003/0139667 A1 * | 7/2003 | Hewko et al. | 600/410 |
| 2003/0139677 A1 | 7/2003 | Fonseca et al. | |
| 2003/0146836 A1 | 8/2003 | Wood | |
| 2003/0149346 A1 * | 8/2003 | Arnone et al. | 600/309 |
| 2003/0153832 A1 | 8/2003 | Zumeris et al. | |
| 2003/0181794 A1 | 9/2003 | Rini et al. | |
| 2003/0181890 A1 | 9/2003 | Schulze et al. | |
| 2003/0195396 A1 | 10/2003 | Scarantino et al. | |
| 2003/0225331 A1 | 12/2003 | Diederich et al. | |
| 2003/0229382 A1 | 12/2003 | Sun et al. | |
| 2004/0015058 A1 | 1/2004 | Besson et al. | |
| 2006/0200012 A1 * | 9/2006 | Mansour et al. | 600/310 |
| 2006/0264760 A1 * | 11/2006 | Liu et al. | 600/473 |

* cited by examiner

FIG. 4A
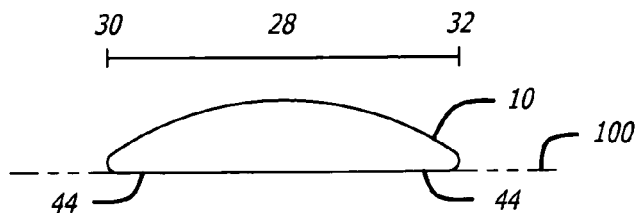
FIG. 4B
FIG. 4C
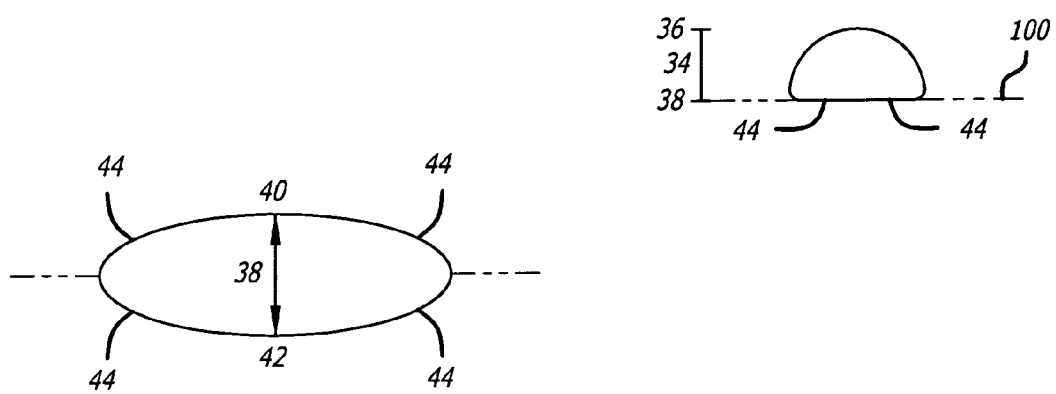
FIG. 4D
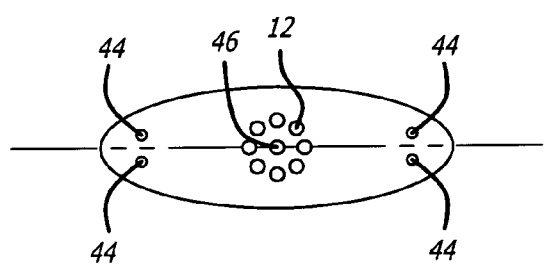
FIG. 4E
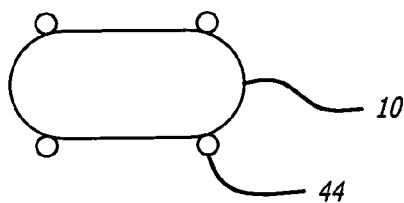

FIG. 5A
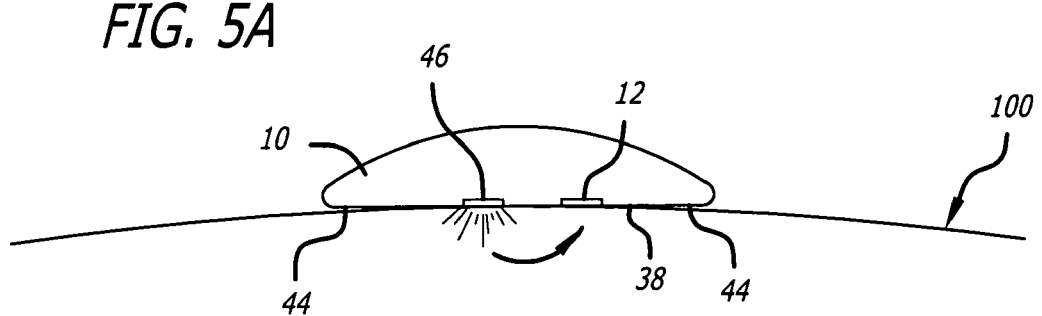
FIG. 5B
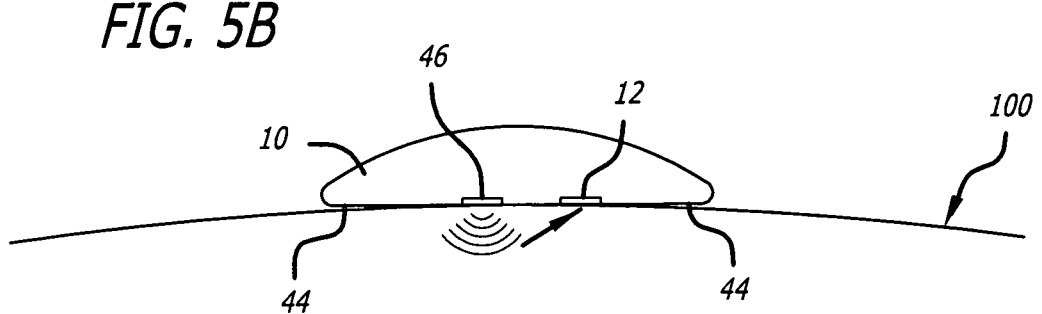
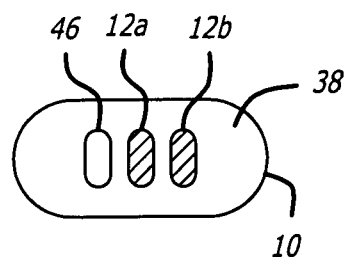
FIG. 5C
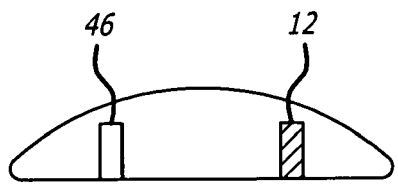
FIG. 5D

IMPLANTABLE DEVICE WITH SENSORS FOR DIFFERENTIAL MONITORING OF INTERNAL CONDITION

CROSS-REFERENCE TO RELATED APPLICATIONS

This application claims priority to U.S. Provisional Patent Application 60/449,963, filed Feb. 26, 2003, and U.S. Utility patent application Ser. No. 10/776,022, filed Feb. 9, 2004, "Surgical Drain with Sensors for Differential Monitoring of Internal Condition," claiming priority to U.S. Provisional Patent Application 60/445,714, filed Feb. 7, 2003, and 60/453,009, filed Mar. 6, 2003 and incorporates the contents of the aforementioned applications in their entirety.

BACKGROUND OF THE INVENTION

1. Field of Invention

The present invention is directed to devices and methods of using devices to monitor internal tissue condition, and more particularly to an implantable device or system having at least two sensors for differential monitoring the condition of a tissue or fluid proximate to the sensors.

2. Description of Related Art

It is desirable for a physician to know the condition of organs, or more generally tissues within the patient's body particularly after trauma or surgical manipulation. Since such tissues may reside under the skin or within a body cavity, a physician must invasively inspect the tissue (such as by surgery, including laparoscopy), or use indirect measures to assess a tissue's condition (such as radiology, blood testing and patient accounts of sensations of illness or pain). However, these methods can be disadvantageous. An invasive examination may cause discomfort and risk of infection to the patient, and the information obtained either through direct inspection or indirectly via blood or radiological analysis, may be relevant only to the time at which the procedure is performed, and examination may render only indirect information about the physiological condition of the tissue.

Monitoring of tissue function can be important after surgeries such as organ transplantation, resection, cryosurgery and alcohol injection. Surgical complications, including tissue rejection, infection, non-specific inflammation, and vascular complications should be monitored. For example, vascular complications, may disrupt adequate oxygen circulation to the tissue, which is critical to organ function and survival. Following liver surgery, for example, a physician may draw patient blood to determine the condition of the organ by measuring liver enzymes (such as transaminases) and clotting factors (such as prothrombin). Unfortunately, these blood tests reflect liver condition only at the time the blood sample is drawn, and changes in these laboratory values can often be detected only after significant organ damage has already occurred, permitting a limited opportunity for intervention by the physician to improve the condition of the organ or find a replacement organ in case of transplantation for the patient.

Early access to information regarding complications would allow early intervention and avoid the need for more invasive procedures such as biopsy, angiogram, nephrogram, etc. and further associated complications. Both early diagnosis of complications and early intervention may improve the chances of therapeutic intervention prior to irreversible damage, tissue survival and decrease the risk of mortality and morbidity in patients, and may also play an important role in reducing the organ shortage and the extra cost and risk of retransplantation.

By further example, intra-abdominal pressure following major surgery or trauma (such as a car accident, gun shot wounds, combat, or earthquake injuries) may rise to extremely high levels due to tissue edema secondary to the injury, especially following multiple blood transfusions, severe shock or inflammatory responses.

An increase in pressure may lead to severe organ dysfunction, such as kidney failure and acute respiratory failure due to lung compression through the diaphragm. The increased pressure in the abdomen may also lead to a decrease in the venous returns to the heart, therefore, affecting the cardiac output and the perfusion to all organs/tissues leading to a decrease in oxygen delivery.

Early detection of critical intra-abdominal pressure may be corrected by several interventions, including sedating the patient or opening of the abdomen. Prompt restoration of proper intra-abdominal pressure can reverse the consequences described above. However, once a critical point is reached, organs may suddenly fail, which may be irreversible in certain conditions and lead to rapid deterioration of multiple organs and potentially death.

One method of monitoring intra-abdominal pressure following major surgery or trauma relies on indirect measurement of intra-organ pressure such as the bladder or the stomach pressure. These methods require direct operator intervention and are done only intermittently at a specific timing, such as every 1 to 4 hours, or if the patient shows signs of deterioration.

Current methods of measuring abdominal pressure may carry significant errors due to direct personal intervention, lack of reproducibility and challenges related to the injury itself. For example, a large hematoma or pelvic fracture may affect the bladder pressure directly without relation to the overall intra-abdominal pressure.

As discussed above, current methods of internal tissue monitoring have significant disadvantages. Therefore, it is desirable to have a device and methods to aid physicians in predicting problems and complications associated with internal trauma or surgery. It is desirable to have a device which is positionable and removable with relatively minimal effort, minimally invasive and causes minimal discomfort for the patient, provides continuous current information about tissue or organ condition, provides direct information about tissue or organ condition, and/or provides feedback on the effects of interventions, such as medications or other procedures to improve tissue or organ condition.

BRIEF SUMMARY OF INVENTION

In one embodiment of the invention, a device may be used for intraoperative and/or postoperative monitoring of the condition of a tissue.

In one embodiment of the invention, a device having at least two sensors may be used to provide continuous differential measurements relating to the physiological condition of a tissue or fluids proximate to a tissue.

In one embodiment, an implantable device may be configured for ease of application by a physician, as well as ease of removal when monitoring is no longer required.

These, as well as other objects, features and benefits will now become clear from a review of the following detailed description of illustrative embodiments and the accompanying drawings.

BRIEF DESCRIPTION OF DRAWINGS

FIGS. 4A-D depict a side view (A), end view (B), plan view (C) and bottom view (D) of one embodiment of a housing used for the implantable device of the present invention; FIG. 4E is a schematic depicting a plan view of one embodiment of an implantable device.

FIGS. 5A-C are schematic diagrams depicting various views of embodiments of an implantable device; FIG. 5D depicts a cross-sectional view of one embodiment of an implantable device including at least one sensor positioned within a housing.

DETAILED DESCRIPTION OF ILLUSTRATIVE EMBODIMENTS

Figure 1A:
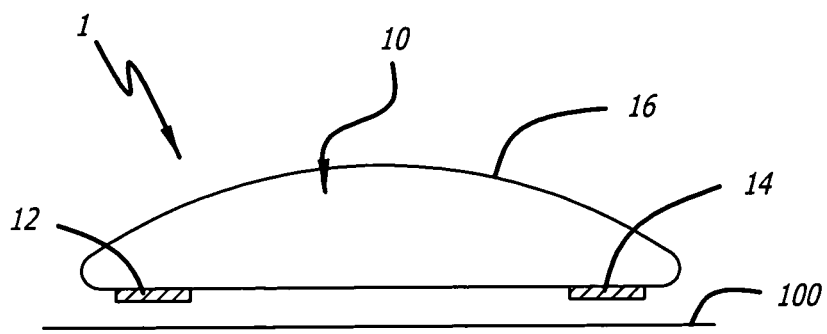
FIGS. 1A-C are schematic diagrams depicting a side view of one embodiment of an implantable device 1 for differential monitoring of tissue conditions.

FIG. 1A is a schematic diagram depicting a side view of one embodiment of an implantable device 1 for monitoring tissue condition. As shown in FIG. 1A, the device 1 may include a housing 10 for implantation within the body proximate to a tissue 100 to be monitored having at least two sensors 12/14. The housing 10 may include a first and second surface on the housing outer side 16. The first sensor 12 may be configured to sense a physiological property of tissue 100 proximate to the first surface; and the second sensor 14 may be configured to sense the same physiological property of tissue proximate to the second surface 100. The device 1 may further include a processing system 24 in communication with the first and second sensors configured to compare a difference between the physiological property sensed by the first and second sensors 12/14.

Figure 1B:
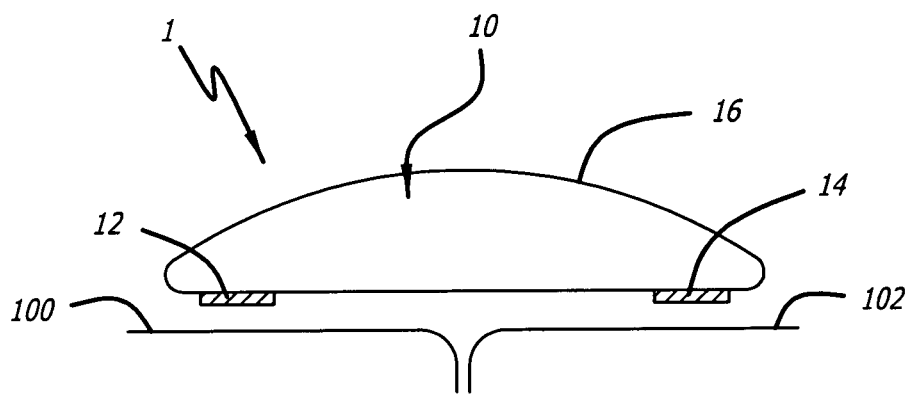

The first and second sensors 12/14 may be positioned at first and second surface which are spaced from one another at a selected distance along the housing length 28. The first and second sensors 12/14 may be positioned at a first and second surface, which are on the same face of the housing 10, such that the first and second sensors 12/14 are proximate to different portions of the same tissue 100, or are proximate to different tissues 100/102 (as shown in FIG. 1B).

Figure 1C:
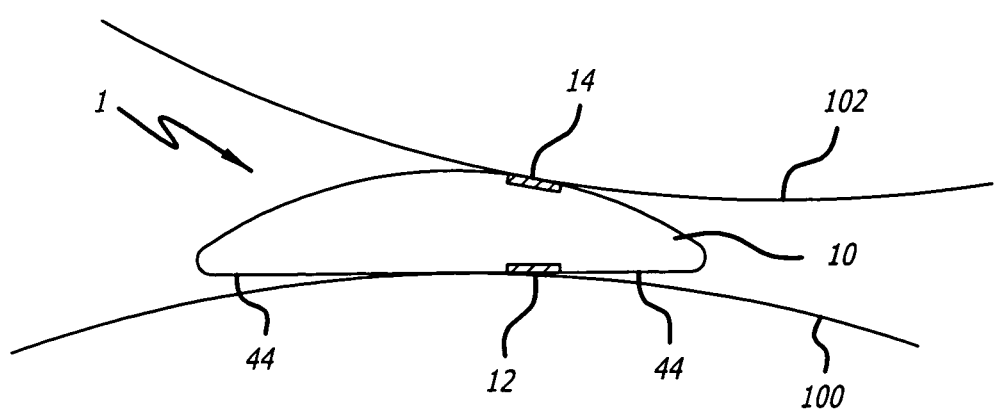

FIG. 1C is a schematic diagram depicting a side view of one embodiment of an implantable device 1 for monitoring tissue condition. As shown in FIG. 1C, the device 1 may include a housing 10 for implantation within the body proximate to a tissue 100 to be monitored having at least two sensors 12/14. The housing 10 may include a first and second surface on the housing outer side 16. The first sensor 12 may be configured to sense a physiological property of tissue 100 proximate to the first surface; and the second sensor 14 may be configured to sense the same physiological property of a different tissue 102 proximate to the second surface. The first sensor 12 may be positioned on a first surface which is substantially opposite to a second surface on which the second sensor 14 may be positioned, such as shown in FIG. 1C.

Figure 1D:
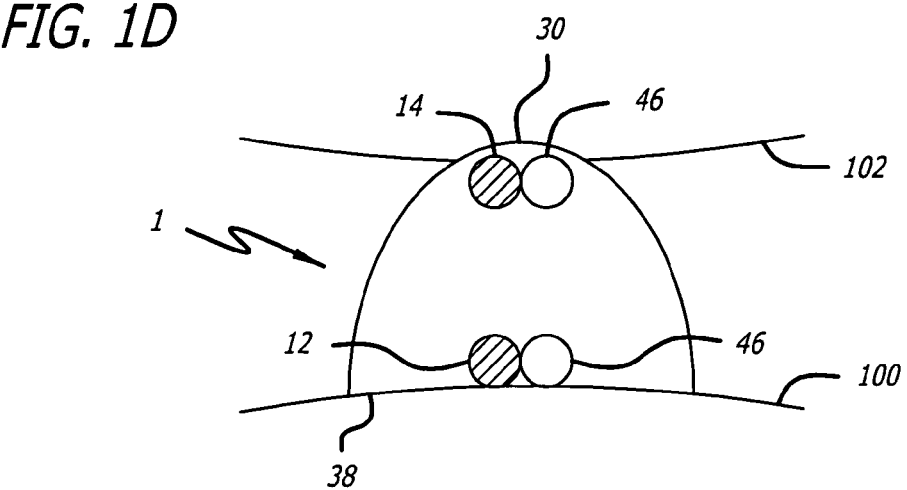
FIG. 1D is a schematic diagram depicting an end view of one embodiment of an implantable device.

FIG. 1D is a schematic diagram depicting an end view of one embodiment of an implantable device 1. In one embodiment of the invention, the implantable device 1 may include at least one pair of sensors 12/14 positioned approximately on opposite sides of the housing 10. Each sensor 12/14 may be proximate to a transmitting element 46, for providing energy to the tissue 100/102 being evaluated.

In use, the implantable device 1, may include at least two sensors 12/14 placed on about opposite sides or proximate to sides of the housing 10 such that the sensor pairs 12/14 may be used to acquire differential measurements between different organs/tissues positioned in the proximity of sensors pair 12/14. For example, as shown FIGS. 1C & 1D an implantable device 1 may be positioned, such that the housing lower surface 38 is proximate to an organ to be monitored 100, and the housing upper surface 36 is proximate to an adjacent tissue 102. Therefore, sensor pairs 12/14 may be positioned to measure a parameter differentially between the monitored tissue 100 and the adjacent tissue 102. These differential measurements may improve the accuracy of the measurements/diagnosis, such as in monitoring for complications in hepatic perfusion. For example, a lower than normal oxygenation of the liver may not be indicative of problems in the hepatic perfusion because the oxygenation of the whole body may be lower than normal due to respiratory and/or circulatory problems. However, if the oxygenation levels of the liver are lower than normal while the adjacent tissues are at normal oxygenation levels, then this is a real indication of reduced hepatic perfusion.

Figure 2:
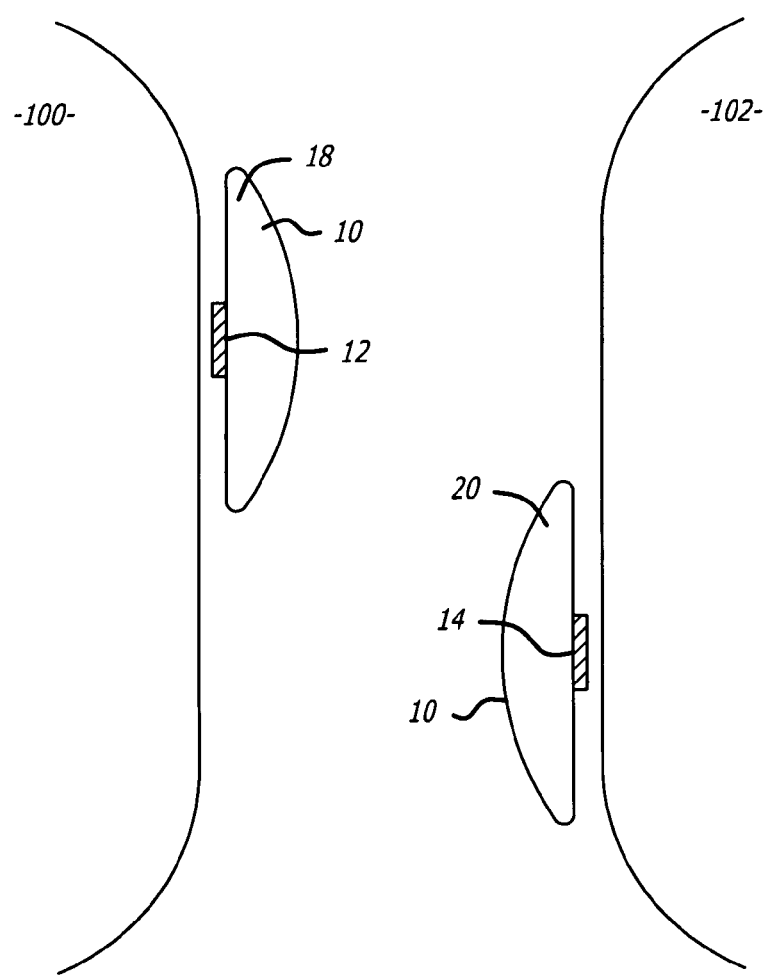
FIG. 2 is a schematic diagram depicting one embodiment of a system showing side views of a plurality of implantable devices for differential monitoring of tissue condition.

FIG. 2 is a schematic diagram depicting one embodiment of a system including a plurality of implantable devices 1 for differential monitoring of tissue condition. As shown in FIG. 2, the system may include a first device 18 including a first housing 10 for implantation having at least one sensor 12 configured to sense a physiological property of tissue 100 proximate to the first device 18. The system may further include a second device 20 including a second housing 10 for implantation having at least one sensor 14 configured to sense the same physiological property of a different portion of the tissue 100, or a different tissue 102 proximate to the second device 20.

The system may further include a processing system 24 in communication with the first and second sensing system configured to compare a difference between the physiological property sensed by the first and second sensing systems.

Figure 3:
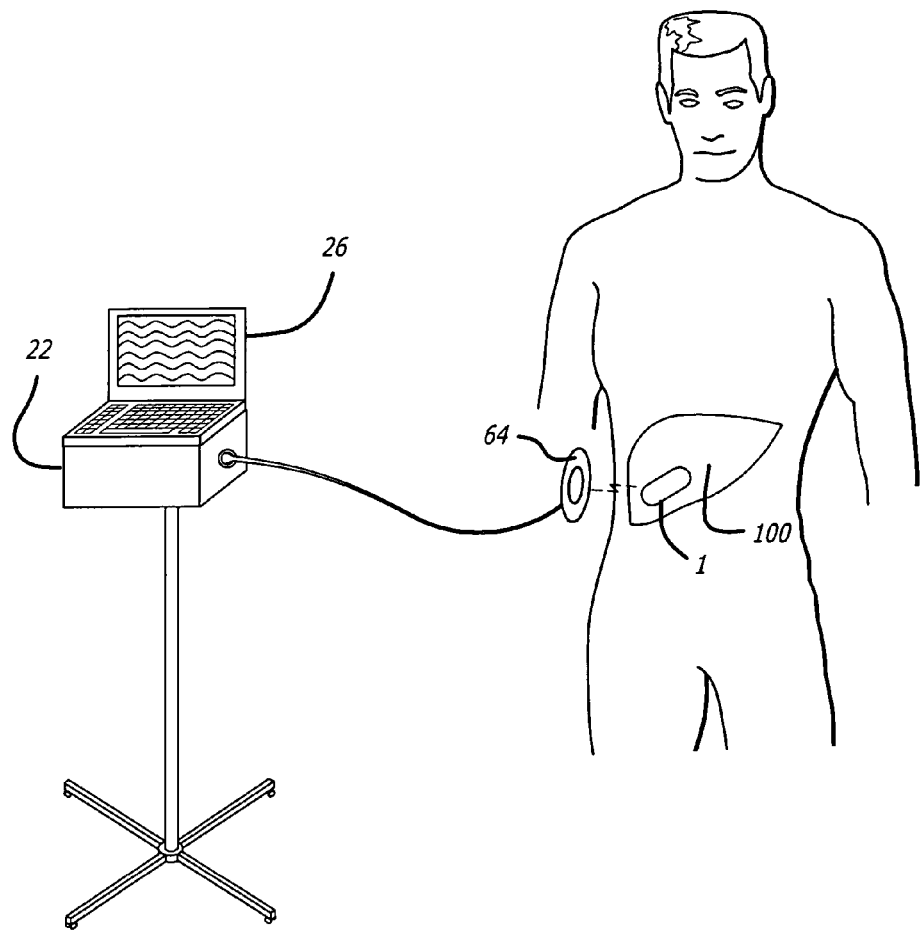
FIG. 3 is one embodiment of a system for differential tissue monitoring including an implanted device including one or a plurality of sensors in wireless communication with an external monitoring system.

As shown in FIG. 3, the implanted device 1 may include one or a plurality of sensors 12/14 in communication with a monitoring system 22 in a wireless manner, described below. The monitoring system 22 may receive, process, display and/or record the information from the sensing systems. The monitoring system 22 may include a processing system 24, and may include a display 26 configured to depict information obtained from the implantable device 1.

FIGS. 4A-D depict a side view (A), end view (B), plan view (C) and bottom view (D) of one embodiment of a housing 10 which may be used for the implantable device 1 of the present invention. As shown, the housing 10 may have a housing length 28, extending from the housing first end 30 to the housing second end 32. The housing 10 may have a housing height 34 extending from the housing upper surface 36 to lower surface 38. The housing 10 may have a housing width 38 extending between the right and left sides 40/42. In one embodiment, the maximum dimensions are about less than 12 mm. The housing 10 may be in the form of any shape including, but not limited to circular, ovular, square, triangular shape. The shape and size of the housing 10 may be selected so it may be inserted and/or removed with minimal invasiveness, such as by laparoscopic surgery or specialized injectors if desired.

The housing 10 may be made of any biocompatible material suitable for implantation within the body. The material may be selected so as to be minimally allergenic, for example. By way of example, the housing 10 may be of a biocompatible ceramics, metals and/or glass, and may be entirely or partially transparent. This may be advantageous in that transmitting and receiving elements 46/12 may be positioned within the housing 10.

In some embodiments, it may be desirable to stabilize the position of the implantable device 1 relative to the tissue 100/102, such that the sensors 12/14 have improved contact and/or increase the likelihood that measurements taken over time will be of the same or similar portion of the tissue 100/102. Therefore, in some embodiments, the housing 10 may be modified.

As shown in FIGS. 4A-D, in one embodiment, the housing 10 may include at least one anchor 44 configured for insertion into a tissue 100 to stabilize the position of the housing 10 within the body. The anchor 44 may be integral to the implantable device 1 or may be fabricated separately from the implanted device 1 and connected thereto. The anchor 44 may be in the form of a biologically compatible needle, which may include a beveled distal end for insertion into a tissue 100.

FIG. 4E is a schematic depicting a plan view of an implantable device 1. In one embodiment, the anchor 44 may be in the form of a tie-loop 44 extending from the housing 10, such as at the lower surface 38. In use, a surgeon may utilize the loop as a suture point to attach the implantable device 1 to a tissue 100, such as with a resorbable suture or staple.

Anchors 44 may be advantageous at least in preventing the housing 10 from moving relative to the organ 100 during use. The form of the anchor 44 may be selected to minimize damage to the tissue to which the implantable device 1 is attached. Further, the anchor 44 may be selected to maximize the stability of the contact between the housing 10 and the target organ 100, yet minimize the effort and damage caused during device 1 removal.

The implantable device 1 may include a sensing system configured to sense a physiological property of a tissue 100/102 proximate to the device 1. The implantable device 1 may include electrical transmitters 46 and/or sensors 12, and/or fiberoptic transmitters 46 and/or sensors 12. In some embodiments, the sensing system may include sensors 12 which are positioned proximate to the device 1 and tissue 100. In some embodiments, transmitting elements 46 and receiving elements 12 may be configured to deliver energy and receive energy, for transmission to another portion of the sensing system to sense a physiological property of a tissue 100. The energy may include, but is not limited to, light, heat and ultrasound. It is to be understood that sensor 12 may refer to either a sensor, such as an electrical sensor, or a receiving element such as a fiberoptic proximate to the housing 10. The sensors 12 may be positioned proximate to a tissue 100 for which monitoring is desired, and the sensors 12 may be configured to receive and/or detect parameters regarding the condition of the tissue 100 or fluid proximate to the tissue 100. The sensor 12 may be situated such that at least a portion of the sensor 12 is in contact with the monitored tissue 100 or in proximity to the tissue 100, or in contact with interstitial fluids therefrom so as to probe the condition of the adjacent tissue 100.

The implantable devices 1 may be configured to sense at least one or more physiological properties of a tissue or the surrounding fluids including, but not limited to: temperature, oxygenation, perfusion, color, pH, respiratory coenzyme NADH prothrombin levels, biochemical composition (such as hemoglobin content, exogenous drug concentrations (including chemotherapeutic agents), and mechanical properties (such as turgidity, stiffness, echogenicity and average separation between scatters).

The receiving elements 12 may be disposed at any configuration about the transmitting element 46. The receiving elements 12 may be disposed at a circular configuration about the perimeter of the transmitting element 46, as shown in FIG. 4D. The transmitting element 46 may be, for example, a light emitting diode (LED) and the receiving elements 12 may be photodetectors with various optical filters to measure radiation in preselected wavelength bands. Alternatively, a single receiving element 12 may be surrounded by multiple transmitting elements 46. The receiving element 46 may be for example a wideband photodetector and the transmitting elements may be light emitting diode (LED) with various emission wavelengths.

FIGS. 5A-D are schematic diagrams depicting various views of embodiments of the implantable device 1. FIG. 5A depicts a side view of one embodiment of a housing 10 including at least one sensor 12 proximate to the housing lower surface 38. The housing 10 may further include at least one transmitting element 46 configured to deliver energy to the tissue 100, including the tissue surface.

In one embodiment, as shown in FIG. 5A, the transmitting element 46 may radiate energy, such as light (including white light) to the monitored tissue 100, in the proximity of the at least one sensor 12. In one embodiment, as shown in FIG. 5B, the transmitting element 46 may radiate energy, such as ultrasound to the monitored tissue 100, in the proximity of the at least one sensor 12. For example, transmitting elements 46 may be a miniature ultrasonic transducer (such as about 1 mm diameter) emitting high frequencies (such as about 20 MHz), and may be operated in the A-mode (amplitude mode) to measure the mechanical and structural properties of the adjacent tissue 102.

FIG. 5C depicts a bottom view of one embodiment of an implantable device 1 including a housing 10, and at least two sensors 12a/b, spaced at a distance from a transmitting element 46 on the housing lower surface 38. In one embodiment, the configuration may be used such that at least one transmitting element 46 transmits energy and the sensors 12a/b receive derivative energy to detect different physiological parameters of the same tissue 100, such as perfusion, oxygenation and temperature. The configuration may be used to measure the same parameter, and may permit the measurement of energy attenuation over distance between the transmitter 46 and the sensors 12a/b which are spaced at a distance from the transmitting element 46 and one another.

FIG. 5D depicts a cross-sectional view of one embodiment of an implantable device 1 including at least one sensor 12 and one transmitter 46 that is positioned further apart from the sensor 12 within the housing 10. This configuration may allow the sensor 12 to detect energy that has traveled through a deeper depth into the tissue 100. This may be a particularly useful arrangement when using high output (e.g., luminance) transmitters for deeper range detection.

By way of example, as shown in FIG. 5 a sensor 12 in proximity to a transmitting element 46 may be used to collect derived energy, including the reflectance or diffuse reflectance from, or transmitted energy through the tissue 100 monitored, or through fluid in proximity to the tissue monitored.

Figure 6A:
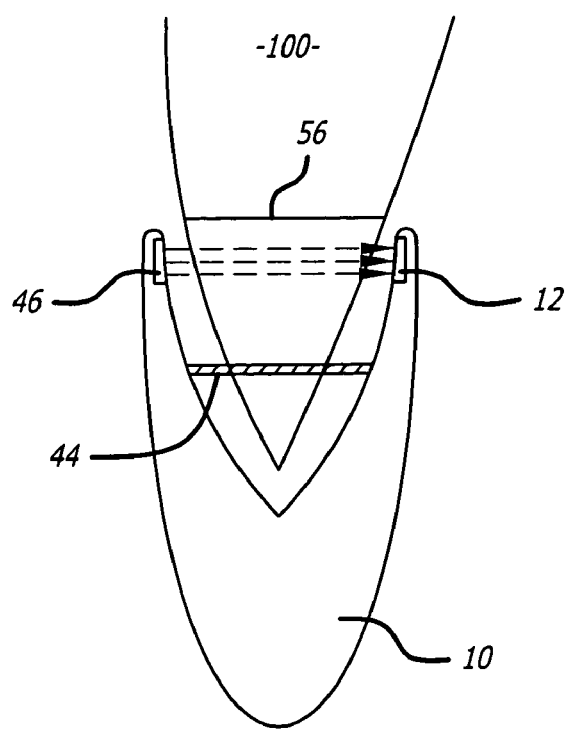
FIG. 6A is a cross-sectional view of one embodiment of a housing, which may be attached by an anchor extending through a portion of the tissue.

In one embodiment, tissue may be placed between a sensor 12 and transmitting element 46 to detect physiological properties by transmission. In one embodiment, as shown in FIG. 6A, the housing 10, may be attached by an anchor 44 extending through a portion of the tissue 100. In one embodiment, measurements can be made between a sensor 12 mounted on approximately the opposite side of the tissue 100 as a transmitting element 46 passing energy through a tissue thickness 56.

Figure 6B:
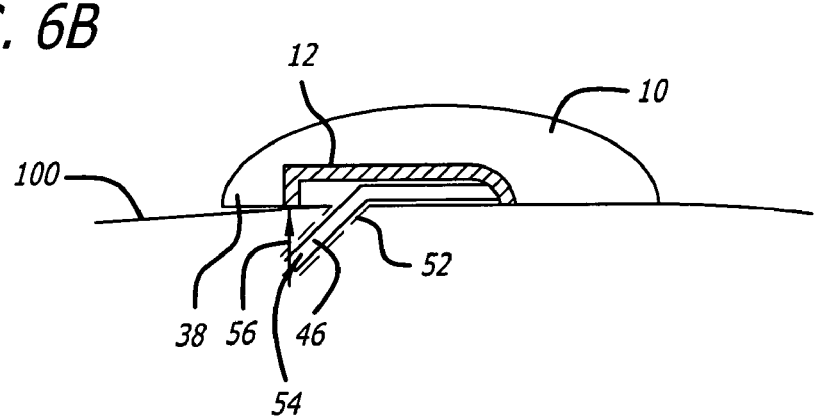
FIGS. 6B and 6C are schematic diagrams depicting cross-sectional views of embodiments of an implantable device.

FIG. 6B is a schematic diagram depicting a cross-sectional view of one embodiment of an implantable device 1, which may include a sensor 12 embedded in the housing lower surface 38 and a transmitting element 46 to be inserted into the tissue 100. The sensor 12 and transmitting element 46 may be fiberoptic or electrical, and the distal ends of each may be oriented such that energy emitted from the transmitting element 46 may be substantially received by the sensor 12. For example, as shown in FIG. 6B the sensor distal end 12 may terminate at a perpendicular to the housing lower surface 38 and the transmitting element distal end 46 may be angled such that the sensor 12 receives energy emitted from the transmitting element 46 distal end. In one embodiment, the distal end of the sensor 12 and the transmitting element 46 may be coaxially aligned.

In one embodiment, the implantable device 1 may include a transmitting element 46 embedded in the housing 10, and a sensor 12 to be inserted into the organ 100. In one embodiment, a casing 52 with a casing lumen 54 may be opposed to or encompass the transmitting element 46 and/or sensor 12 that is being inserted into the organ 100 to provide structural support. The casing 52 may be a hollow needle made of a biologically compatible material. The casing 52 may advantageously serve as an anchor 44 to attach and/or immobilize the implantable device 1 relative to an organ 100.

Figure 6C:
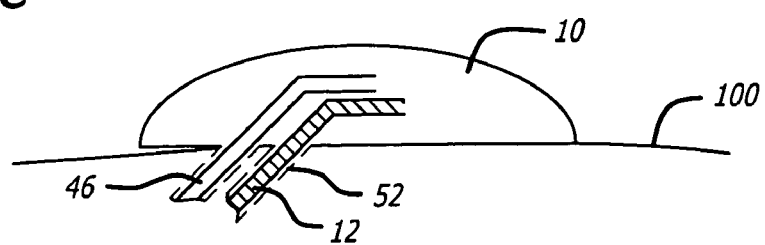

FIG. 6C is a schematic diagram depicting a cross-sectional view of one embodiment of the invention, which may include optical transmission sensors composed of two needle shaped fiberoptics 12/46 for insertion into a monitored tissue 100. For example, as shown in FIG. 6C, the transmitting element distal end 46 and sensor distal end 12 may be angled such that the sensor 12 receives radiation emitted from the transmitting element 46. In one embodiment, the transmitting element 46 and sensor 12 may each be opposed to or encompassed by a casing 52 to provide structural support.

Figure 6D:
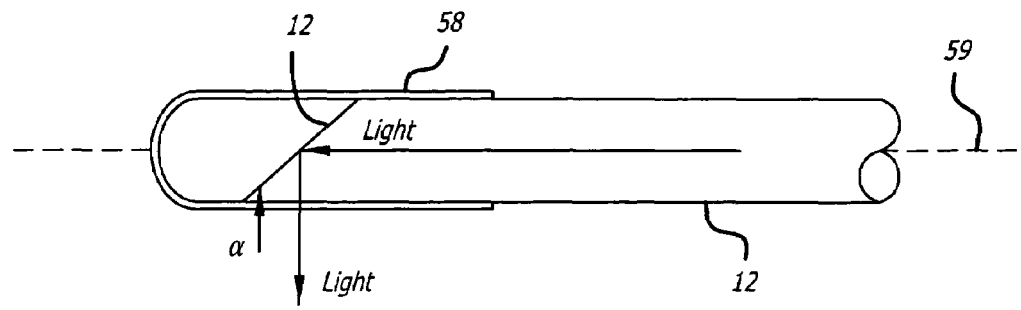
FIG. 6D is a cross-sectional view of one embodiment of the invention, whereby a fiber distal end may be polished at an angle to its axis.

As shown in FIG. 6D, in one embodiment, to enable a fiber to irradiate energy at about 90 degrees, the fiber distal end 12 may be polished at about a 42 -degree angle ($\alpha$) to its axis. Further, a glass ferrule cap 58 may be placed over the polished end. In use, the light may be reflected on the polished end, and be emitted at about 90 degrees to the fiber axis 59. In one embodiment, a fiber collecting or receiving energy may be prepared using a similar process.

In these configurations, for example, light emitted from a transmitting element 46 may be transmitted through a tissue thickness 56 to a sensor 12. Using standard transmission, reflection and/or fluorescence spectroscopy techniques, the transmitted light may be used to collect data related to physiological information.

Any type of sensors 12 (such as oxygenation, perfusion, pH, temperature, color) may be used in a differential mode measurement, such as described above. The sensor 12/14 type used may be selected so as to maximize the detection of the desired physiological parameter, maximize biological compatibility with the patient's tissues or other components of the device 1, and to minimize any risk of leak electrical currents or the like.

The system may acquire simultaneous differential measurements from along the housing length 28 or between the different tissues 100/102 between which the device 1 is positioned. Measurement of a given parameter simultaneously from adjacent normal organs/tissues 102 (e.g., abdominal wall) and from the organ/tissue of interest 100 (e.g., the liver) can provide a control or reference value. This control or reference value can be used as a comparison factor to improve the accuracy of the parameter measured from the organ/tissue of interest 100.

In one embodiment, the oxygenation of an organ may be determined by measuring the oxygenation of the hemoglobin within a tissue. The spectral characteristics of hemoglobin are dependent on its state of oxygenation. The oxygenation of the organ 100 may be determined by measuring the spectral characteristics of hemoglobin using a similar sensor 12, as described above. Oxygenation levels between tissues 100/102 may then be compared.

In one embodiment, the device 1 may be configured to detect the color of an organ 100. The implantable device 1 may use a single fiber, or may include at least one transmitting element 46 and at least one sensor 12. The transmitting element 46 may be a fiberoptic having a distal end configured to deliver light from a light source to the organ 100. The light may be reflected from, diffusely reflected from or transmitted through at least a portion of the organ 100 in the proximity of the transmitting element distal end 46. The sensor 12 may be a fiberoptic 44 having a distal end configured to collect light having a spectral pattern reflected, diffusely reflected or transmitted through the organ 100, and transmit the spectral pattern to a photodetector or processing system 24. The color may be extracted from a wavelength spectrum using common wavelength to RGB conversion techniques.

The monitoring system 22 may include a processing system 24 for converting the spectral pattern information to a color, which may be presented to a physician on a display 26. The processing system 24 may also convert the spectral pattern information to a color index number, which may be presented to a physician on a display 26. The system may also include data of colors detected from adjacent tissue 102 for comparison, normal colors and color indexes for automatic or manual comparison so that a tissue abnormality may be noted.

Determining the physiological conditions, such as color and/or color index of the tissue, may be advantageous at least in that the physician may determine from the color of the tissue the general health of the tissue, including whether the tissue is adequately oxygenated and/or diseased (e.g., jaundiced). Further, the monitoring function is advantageous in that it may be continuous or at intervals selected. Further, the monitoring function is advantageous in that is may be minimally invasive and does not require opening the patient to assess the tissue condition.

In one embodiment, diffuse reflection may be used to determine the oxygenation level of at least a portion of an organ 100. This method may be advantageous at least in that information about the internal portion of the organ 100 may be obtained, without penetrating the surface of the tissue with a sensor 12 or a transmitting element 46.

In one embodiment, the device 1 or system may be configured to detect the temperature of the monitored organ 100. In one embodiment, the device 1 may include a fiberoptic temperature sensor 12. For example, a fiberoptic thermometer may be used. The fiberoptic may transmit an excitation light pulse to the fiber distal end in proximity to a tissue 100, causing it to fluoresce. The fiber distal end may include a nonconductive phosphor tip. The fluorescent signal may be transmitted back to a photodetector by the same fiber. The fluorescent decay time may be measured by a multipoint digital integration decay curve, used to correlate the decay curve with a temperature value. The same process may occur relative to an adjacent tissue 102 at approximately a similar time.

The temperature sensor 12 may transmit the light for information processing. A processing system 24 may convert the phosphorescence decay-time to a temperature value, which may be presented to a physician on a display 26. The system may also include data of temperatures detected at adjacent tissue 102 for determination of differences, and normal temperatures for automatic or manual comparison so that an abnormality may be noted. Determining the temperature of the organ 100 is advantageous at least in that the physician can determine from the temperature the general health of the tissue including whether the tissue is being properly perfused after transplant as improperly perfused tissues may decrease in temperature, for example. A temperature sensor 12 may be of any type other than fiberoptic including thermistors, thermocouples and resistance temperature detectors (RTD's), for example.

In one embodiment, the device 1 or system may be configured to detect the respiratory coenzyme NADH levels from the monitored organ 100 and adjacent tissue 102. Fluorescence spectroscopy may be used to measure the fluorescence of NADH which has a peak emission at 470-nm and to detect its concentration in the tissue 100, and adjacent tissue 102 for comparison.

In one embodiment, the device 1 or system may be configured to detect concentrations of exogenous drugs within the tissue 100 or fluid. For example, drugs (such as chemotherapeutic agents) may auto-fluoresce or may be coupled with a fluorescing tag having a selected peak emission, which may be detected by fluorescence spectroscopic methods.

By way of example, pH sensors 12 may be used to detect changes in ion concentration in fluids surrounding tissues 100/102 or within a drain lumen 32. For examples of pH sensors 12 that may be useful in this invention, see U.S. Pat. No. 5,916,171 to Mayviski, herein incorporated by reference.

In one embodiment, a pressure sensing system may be used to detect the pressure within a body cavity, such as the abdominal cavity. For example, a fiberoptic pressure sensor 12 may be used, and may include a pressure sensing element such as an optical interferometer at a distal tip of a fiber, and interferometric integration may be used to sense and monitor pressure over time at tissues 100/102. For examples of integration methods, see U.S. Pat. Nos. 5,392,117 and 5,202,949, herein incorporated by reference.

In one embodiment of the invention, the implantable device 1 may include a power source, such as a rechargeable battery. In one embodiment of the invention, the implantable device 1 may be in wireless electromagnetic and/or ultrasonic coupling with an external device which may provide power and/or control signals.

Figure 7:
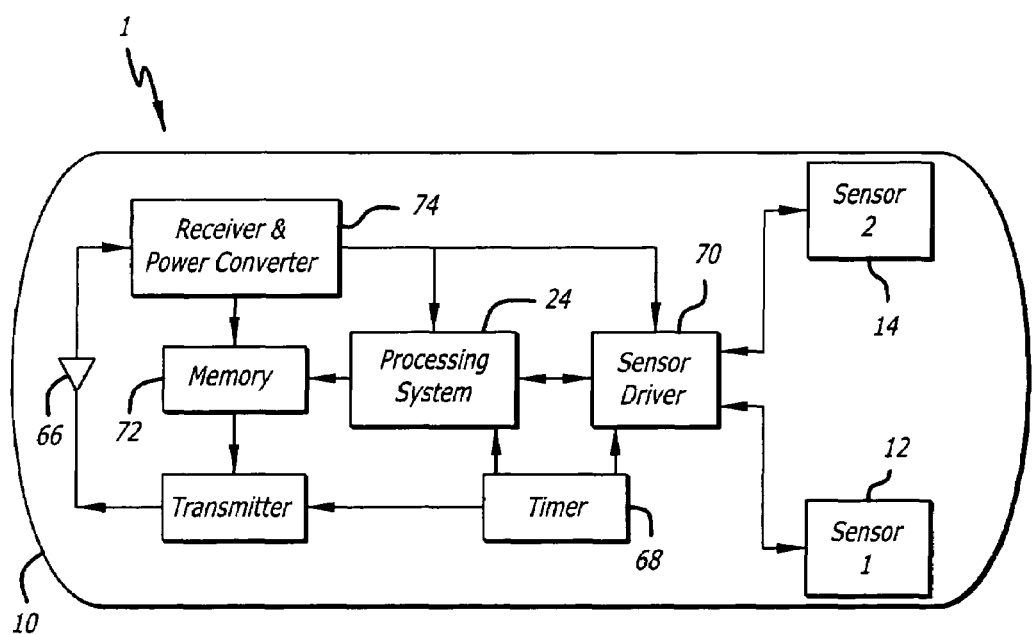
FIG. 7 is a block diagram of one embodiment of an implantable device including an antenna.

For example, as shown in FIG. 3, the implantable device 1 may communicate via telemetry with an external device including an external antenna 64. The external antenna 64 may be of the coil type and may be placed in proximity to the patient at a location near the implantable device 1. The external antenna 64 may be used to induce power to the implantable device 1, for example by transmitting an electromagnetic signal to the device 1. As shown in FIG. 7, the device 1 may include an internal antenna 66 to receive the electromagnetic signal and convert it to current, and may further include components for rectifying current to DC current for storage in the rechargeable battery or use by the device 1.

The external antenna 64 may also be used to transmit control signals to the implanted device 1, such as the frequency at which tissue monitoring should occur. The internal antenna 66 may be used to transmit data signals regarding tissue conditions to the external antenna 64 for communication with the monitoring system 22.

FIG. 7 is a block diagram showing components of one embodiment of the implantable device 1, which may be used. In one embodiment, the implantable device 1 may be set to acquire sensor measurements from the tissues 100/102 at preselected periods of time (such as at about 1-hour intervals) throughout the physician designated monitoring period. The device 1 may include a timer 68 including a pre-set interval at which a sensor driver 70 may be activated to obtain data via sensors 12/14. The sensor measurements or processed data may be saved into a memory 72 (such as a nonvolatile memory) within the housing 10 until requested by the monitoring system 22. To retrieve the stored information from the implantable device 1, the external antenna 64 may be placed near the body surface proximate to the location of the implanted device 1 (see FIG. 3). The external antenna 64 may generate a coded magnetic field that is transmitted through the body and detected by the internal antenna 66. The signal received by the internal antenna 66 may communicate with a receiver 74, which may result in: (1) acquiring a measurement from the tissues 100/102, and (2) transmitting the present and perhaps previous measurements stored in the memory 72 to the monitoring system 22. The transmitted measurements may be received by the external antenna 64 which may be in communication with the monitoring system 22 and processed to determine the tissue condition. A transmit on-demand data transfer protocol may allow the implanted device 1 to conserve power while minimizing the body exposure to unnecessary electromagnetic radiation. Under this transmit on-demand data transfer protocol, the data may be transmitted only when the processor 24 detects an abnormality in the physiological parameters measured by the sensors 12 and/or 14 from the tissues 100 and/or 102.

The general principles of telemetry between internal devices and external components have been described, such as in U.S. Pat. No. 5,193,539, issued Mar. 16, 1993 to Schulman et al., and incorporated herein by reference.

In one embodiment, the implanted device 1, may also include a processing system 24 for receiving information from a sensor 12/14, and processing information, at least in part, prior to transmitting the information to the monitoring system 22.

Figure 8:
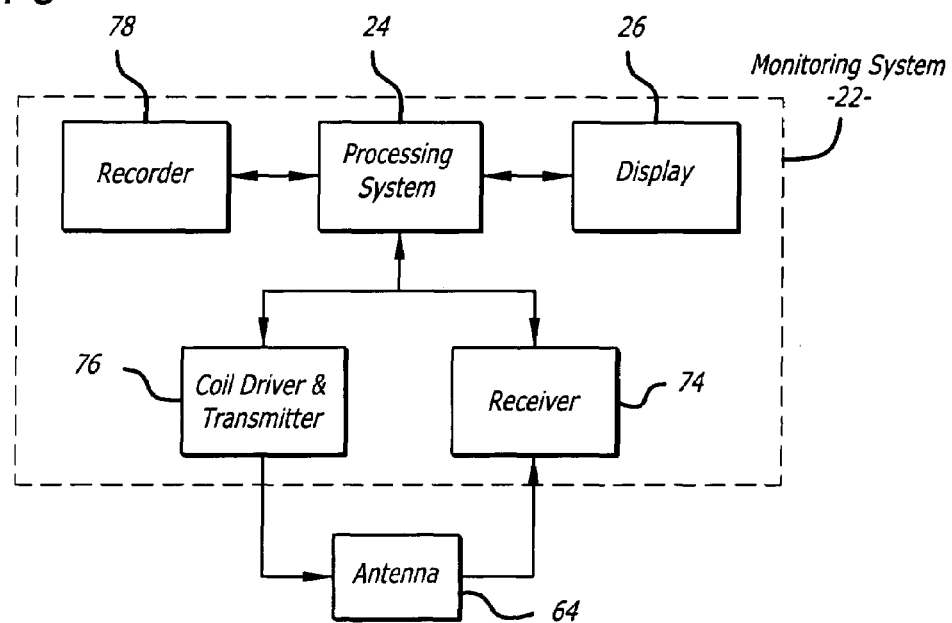
FIG. 8 is a block diagram of one embodiment of a monitoring system for use in the invention.

FIG. 8 depicts one embodiment of a monitoring system 22. In one embodiment of the invention, a system may include at least one implantable device 1 having sensors 12 and 14 in communication with a monitoring system 22 that may include a processing system 24, a display 26, a coil driver and data transmitter 76 which, in addition to transmitting electromagnetic energy to power the implantable device 1 or recharge its battery, may direct the frequency and/or magnitude of signals to transmitting elements 46 and/or receive and detect information from sensors 12, and/or a recorder 78. The monitoring system 22 may also include an external antenna 64 in communication with the implantable device 1.

The processing system 24 either within the implantable device or monitoring system may calculate the difference between values detected by the first and second sensing systems.

The monitoring system 22 may be configured so as to continuously obtain information regarding the condition of the organ or obtain information only at preselected intervals or on demand from a physician. In one embodiment of the invention, the recorder 78 may store acquired information for later retrieval and review. The recorder 78 may be a hard disk of a processor or computer, for example. Extended history (e.g., 7 days) of a given physiological parameter may be stored and later retrieved from the recorder 78, and displayed if desired.

The processing system 24 may include algorithms for comparing the difference between the physiological property sensed by the first and second sensing systems. These differential measurements may improve the accuracy of the measurements, such as in monitoring for complications in hepatic perfusion. For example, a lower than normal oxygenation of the liver may not be indicative of problems in the hepatic perfusion because the oxygenation of the whole body may be lower than normal due to respiratory and/or circulatory problems. However, if the oxygenation levels of the liver are lower than normal while the adjacent tissues are at normal oxygenation levels, then this is a real indication of reduced hepatic perfusion.

The processing system 24 may include signal-processing algorithms to automatically detect and alarm for abnormalities, such as variations in the relative values between the tissue 100 and adjacent tissue 102. In one embodiment, the system may include an alarm which may be triggered when an abnormality is detected in a physiological parameter (relative to pre-set values) or when inadequate contact of sensors 12 to make a measurement. The system may include a manual preset of the alarm threshold.

Figure 9:
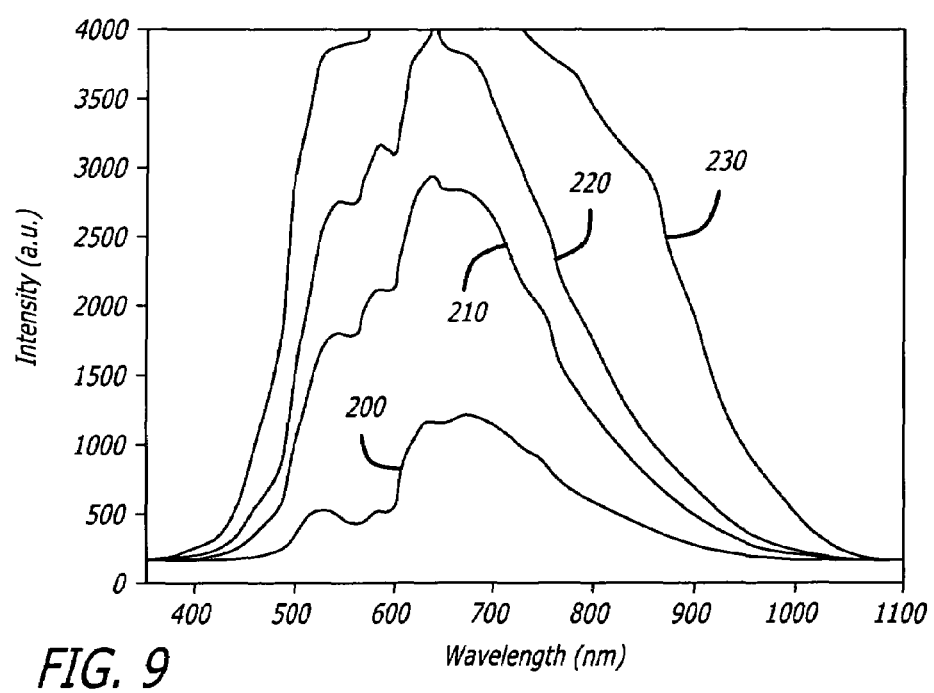
FIG. 9 is an example of a reflectance spectrum of white light from the surface of a deoxygenated liver.

In one embodiment of the invention, the processing system 24 may process the reflectance intensities received from the sensing system at about 540, 580 and 640 nm to determine if a reflectance sensor 12 is in optimal contact with an organ 100. FIG. 9 shows one example of the reflectance spectrum of white light from the surface of a deoxygenated liver. For example, spectrum 200 may result from a reflectance sensor 12 that is in good contact with the surface of the liver. Spectra 210, 220 and 230 may result from a sensor 12 that is not in contact with the liver. The processing system 24 may evaluate the spectrum obtained, and communicate when a sensor 12 is not in good contact with tissue 100.

The system may be configured to permit a physician to be able to review previously recorded data simultaneously while the monitoring system 22 is recording. The system may include a search feature, such that a physician may display the data segments where selected physiological information occurs, such as periods where abnormalities were detected (e.g., hypoxia or ischemia).

FIGS. 10A-E are graphic representations of various modes of one embodiment of a display 26. In one embodiment, the display 26 may include a touch-screen graphic user interface 82. For example, the interface 82 may permit a user to select options, including but not limited to history review of the information detected for a selected parameter, review of abnormal conditions, select alarm option, freeze screen option, trace display option, sample interval selection, display mode. In one embodiment, the physician may select an interval at which measurements are obtained from the tissue. This interval may vary, for example from about 1 to 60 minutes, such as about 5 minutes.

The transmitting element 46 shown in FIG. 4D may be for example a white or a multi-wavelength light emitting diode (LED) and the receiving elements 12 may be photodetectors with various optical filters to measure radiation at preselected wavelength bands. The processing system 24 may control the sensor driver 70 to activate the LED and simultaneously use the filtered photodetectors to measure the returned radiation.

Alternatively, the receiving element 12 may be a single broadband photo detector surrounded by an array of transmitting elements 46 which may be a light emitting diode (LED) with various emission wavelengths. The processing system 24 may control the sensor driver 70 to activate the LEDs sequentially or in various combinations to produce radiation at the wavelengths of interest. Simultaneously, the processing system 24 controls the sensor driver 70 to activate the broadband photo detector to measures the returned radiation.

In one embodiment, a measured spectrum of the light (such as diffusely reflected) may be corrected for distortions caused by the dark current, ambient light and/or spectral response of the system. The measured spectrum of the light may be processed by the processing system 24 according to the known methods of diffuse reflectance spectroscopy (or transmission or fluorescence spectroscopy methods if applicable) for the measurement of the concentrations of oxygenated and deoxygenated hemoglobin in an organ 100. The spectral classification methods may include peak ratios, artificial neural networks (ANN), multiple linear regression (MLR), principal component regression (PCR), and partial least squares techniques (PLS).

In one embodiment, standard methods for converting wavelength to visual red, green, blue ("RGB") may be used to regenerate a color corresponding to the spectra collected from the organ 100 and/or adjacent tissue 102 for visualization on a display 26 of the monitoring system 22. The wavelength to color transformation formula and the color display algorithm values may be calibrated using colorimetry techniques to ensure that the displayed color is visually similar to the actual color of the tissues 100/102.

In one embodiment, spectral information obtained regarding the tissue 100 and adjacent tissue 102 may each be converted to a color index, such as a number for visualization on a display 26 of the monitoring system 22. A numerical color index may be displayed to provide the physician with a quantitative color evaluation of the organ 100 and adjacent tissue 102. This may be advantageous at least in diagnosing tissue conditions, which affect the color of the organ 100, such as jaundice and ischemia. The ratio or difference between the numerical number index of the tissue 100 and adjacent tissue 102 may also be displayed.

Figure 10A:
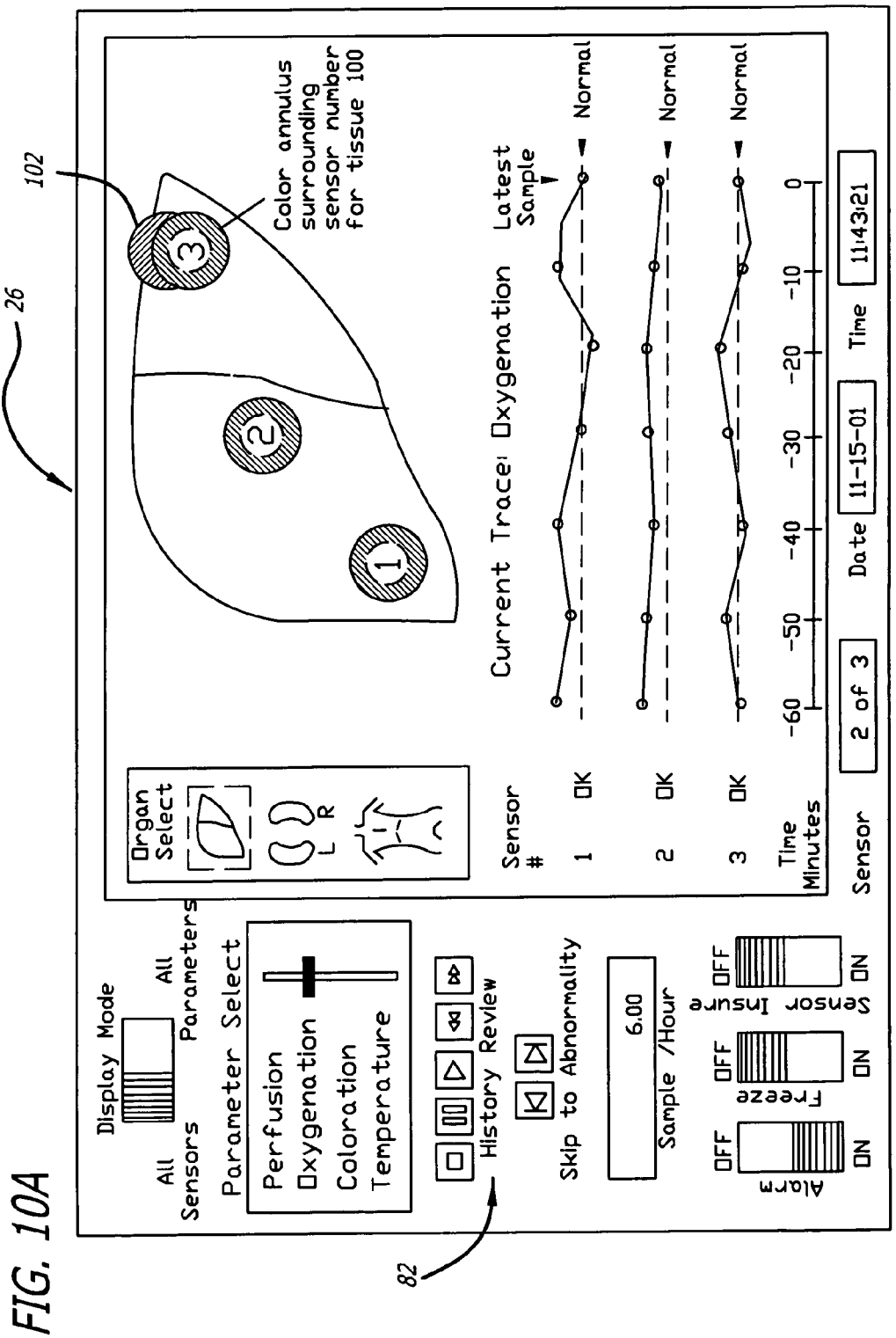
FIGS. 10A-E are graphic representations of various modes of one embodiment of a display.

A display 26 may show information, for example in a graphical, numerical or color form to a physician of user-selected physiological parameters including, but not limited to, tissue oxygenation, perfusion, temperature, coloration, pH and pressure. In FIG. 10A, for example, the display 26 may include a screen showing at least one selected parameter for an implantable device 1 positioned on the organ 100 (such as "1," "2" or "3") over a selected time. In this example, oxygenation levels are shown graphically over time, and corresponding patches of color of the organ 100 and surrounding tissue 102 are depicted on a graphical symbol of the selected organ relative to the position of each implantable device 1.

The color patch may be depicted as an annulus surrounding the implantable device number from which the color is detected.

Figure 10B:
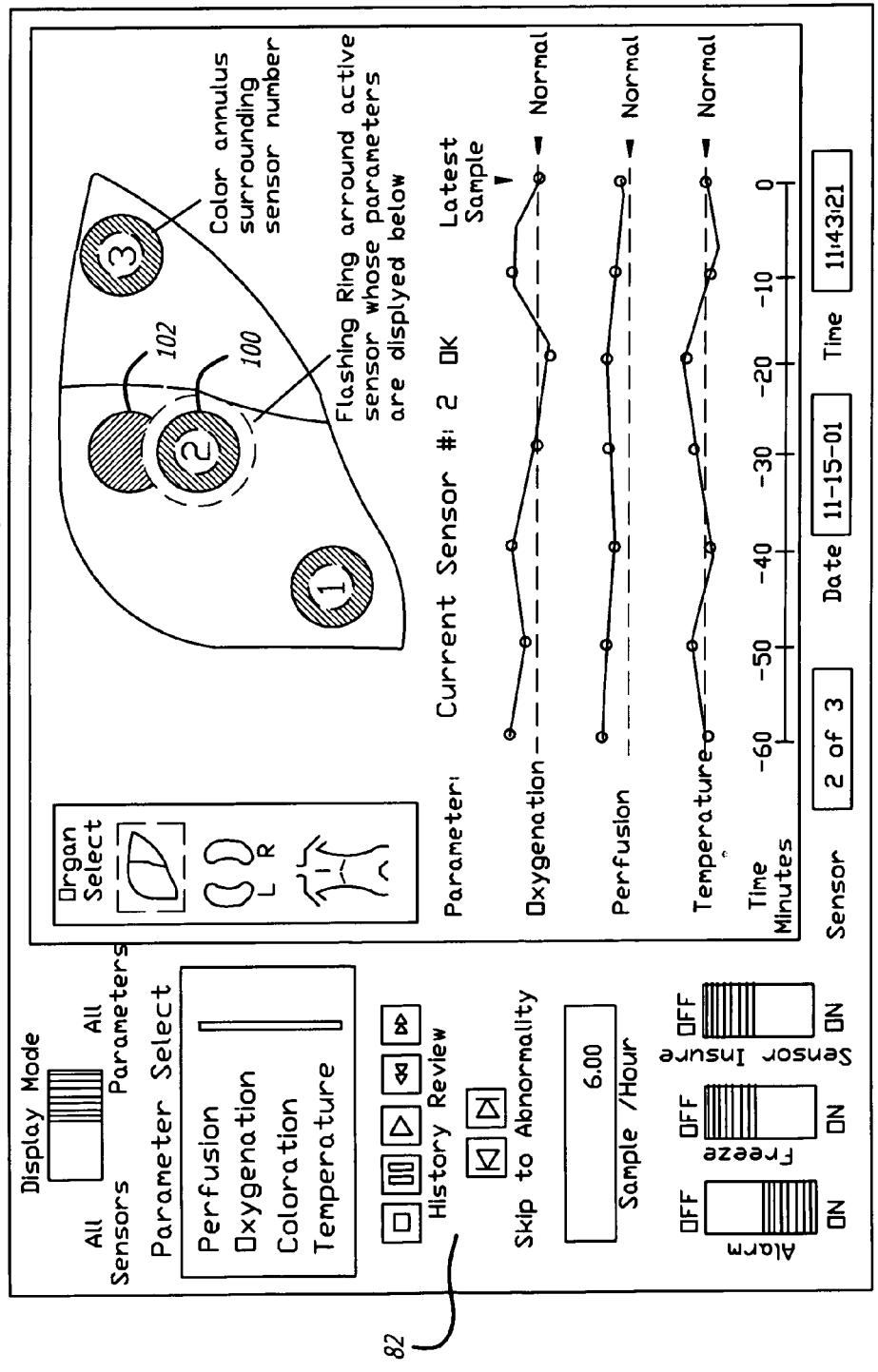
Figure 10C:
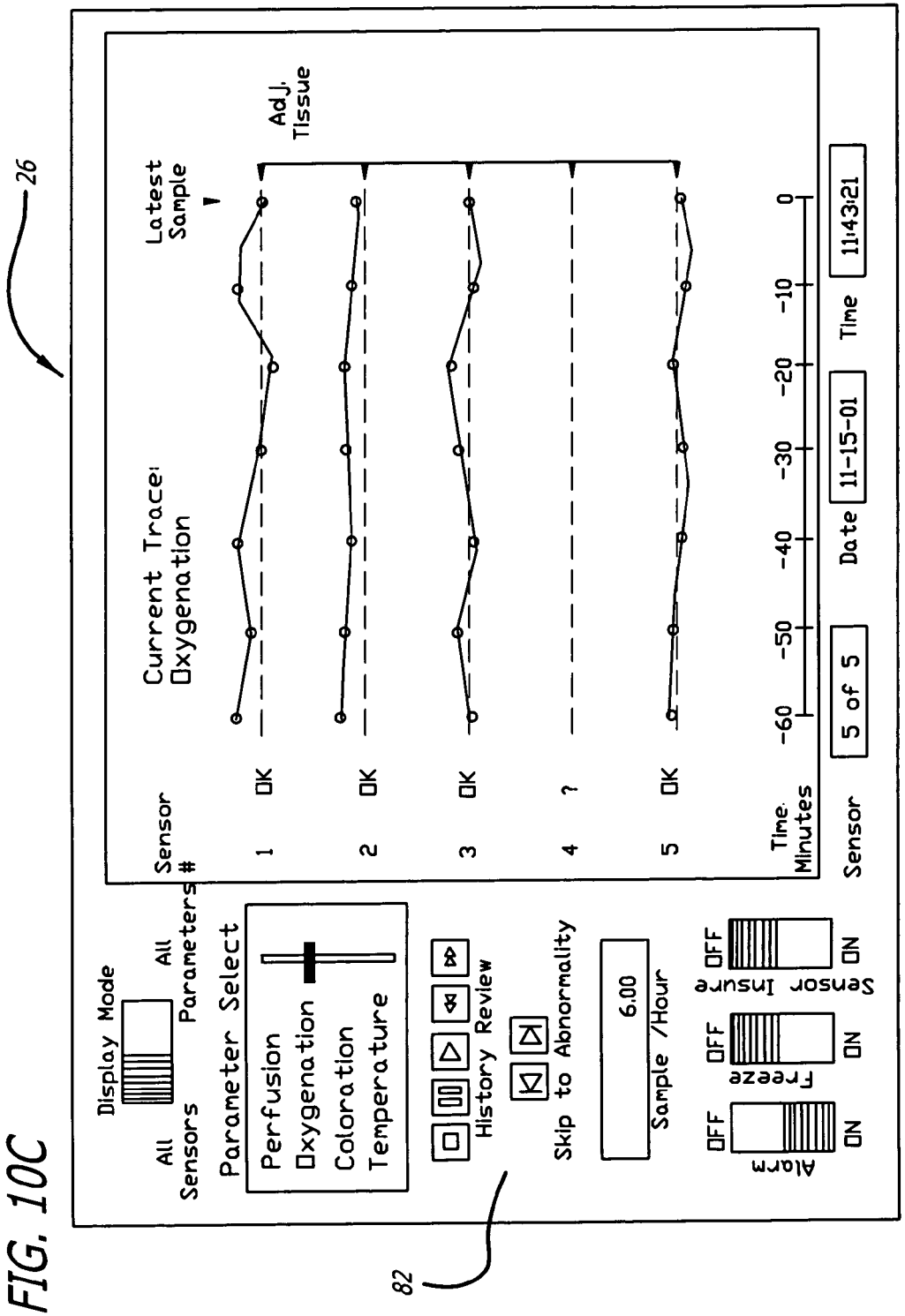

In FIG. 10B, for example, the display 26 may include a screen showing a plurality of different parameters for a single implantable device 1 positioned between the organ 100 and adjacent tissue 102 over a selected time. In this example, oxygenation, perfusion and temperature levels are shown graphically over time, and the corresponding patch of color is depicted on a graphical symbol of the selected organ relative to the implantable device (e.g., "2") for which the information is being displayed. The color patch may be depicted as an annulus surrounding the implantable device number from which the color is detected. A screen indicator may mark the implantable device number from which the displayed oxygenation, perfusion and temperature values were collected. The operator may select to display the parameters set of any implantable device 1 by simply clicking on the symbol of that implantable device on the touch screen.

The physiological parameter detected by each implantable device (such as perfusion or oxygenation of the tissue at the location of each implantable device 1) may be visualized on a display 26 as percentage of predetermined normal values or the adjacent tissue values. The traces may depict the measurements obtained from tissue 100, adjacent tissue 102, or a ratio thereof. For example, the display 26 shown in FIG. 10C displays the oxygenation traces of three implantable devices in various locations relative to the organ 100 relative to adjacent tissue values.

Figure 10D:
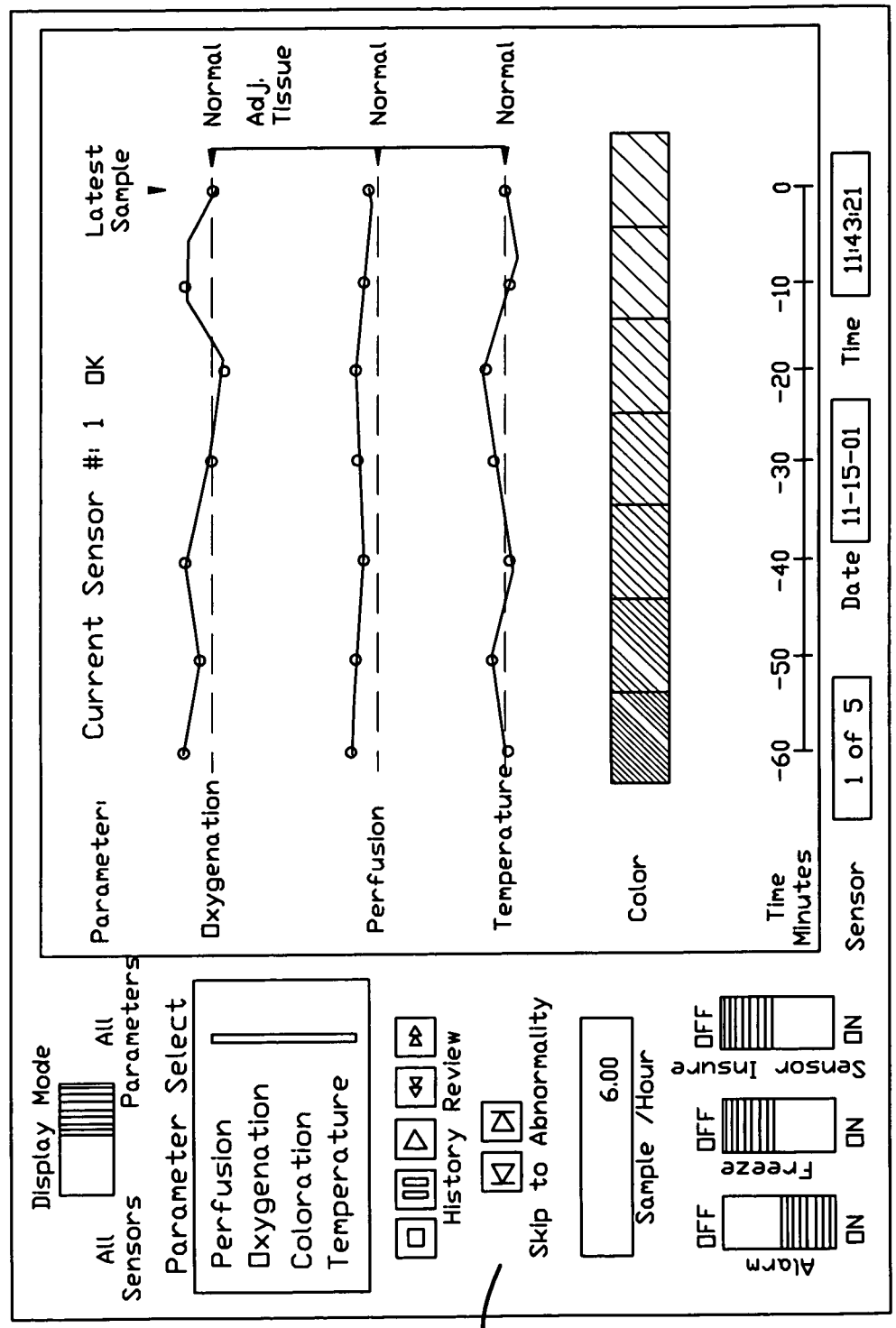
Figure 10E:
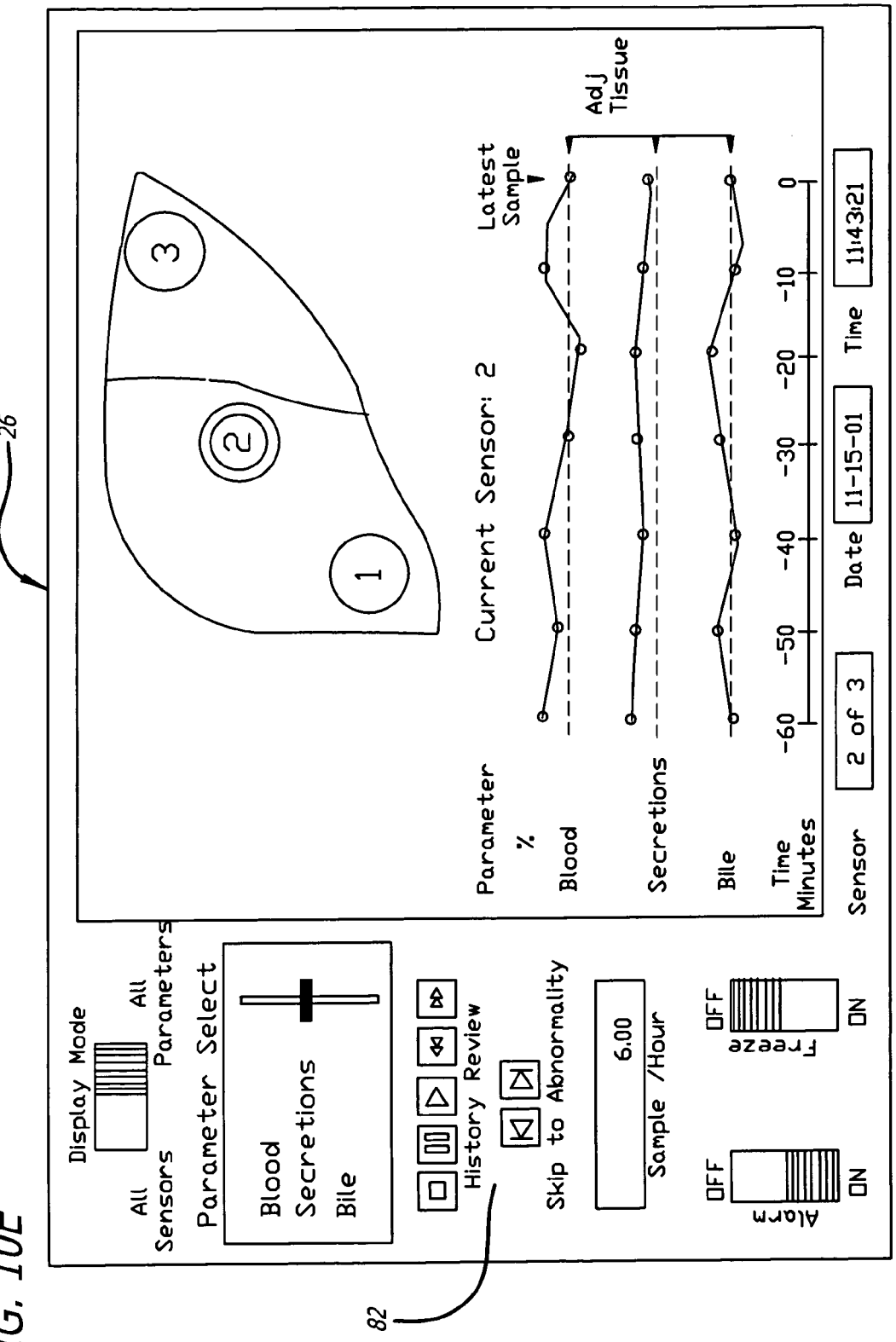

FIG. 10D is a schematic depiction of one embodiment of a display 26. In one embodiment, the physician may select to display different physiological parameters measured at each implantable device location, as shown in FIG. 12D. The display 26 may be configured such that multiple screen windows may be opened to display different implantable device locations at the same time.

The display 26 may include a movable implant-shaped screen cursor that may be freely oriented on a graphical symbol of the human abdomen to show the physician the actual implant orientation inside the body. The implant-shaped cursor may be manually oriented upon the application of the implant.

In one embodiment, an implantable device 1 may be placed in the proximity of an organ 100 which has been transplanted, such as a liver, kidney, such that the housing 10 having a sensor 12 is positioned over at least a portion of the organ 100. This embodiment may be advantageous at least in allowing a physician to monitor the condition of the transplanted organ from the time of surgery through recovery to determine the condition of the organ 100. A physician may use information about the condition of the organ to decide if any further intervention, such as drug treatment (such as antibiotics or immunosuppressants) or retransplantation may be required. This method of monitoring may be advantageous at least in that it may minimize procedures to inspect the organ, enabling detection of organ dysfunction at an early stage, which may allow therapeutic intervention prior to reversible damage, increase implant survival, decrease mortality rate (from infection, organ rejection), decrease the number of organs used for retransplantation, and the additional risk and cost of retransplantation.

In use, an implantable device 1 may be placed within a body cavity proximate to a site of trauma or surgery. To position an implantable device 1, a physician may, for example, create an incision through which the implantable device 1 may be implanted, such as via laparoscopic surgery, upon or within a tissue. Alternatively, if the patient has been opened for surgery, the implants may be positioned proximate to the surgical site, upon or within a tissue, and the body closed around it. The implantable device 1 may be positioned upon an organ 100 or between tissues of interest 100/102, and may be positioned such that sensors 12 contact different regions of a tissue 100/102 until monitoring is no longer needed, at which time the implantable device 1 may be removed from the body. Monitoring from the device 1 may begin intraoperatively, continue post-operatively and cease when physician monitoring is no longer desired.

While the specification describes particular embodiments of the present invention, those of ordinary skill can devise variations of the present invention without departing from the inventive concept. For example, it will be understood that the invention may also comprise any combination of the embodiments described.

Although now having described certain embodiments of methods and implantable devices and system, it is to be understood that the concepts implicit in these embodiments may be used in other embodiments as well. In short, the protection of this application is limited solely to the claims that now follow.

We claim:

1. A method of monitoring the condition of a tissue comprising:
    receiving information from a first sensing system and a second sensing system, wherein the first and second sensing systems are configured to sense a physiological property of a tissue;
    processing information from the first and second sensing systems to compute a difference in information sensed by the first and second sensing systems;
    displaying data on a display regarding the difference between the information received from the first and second sensing systems;
    positioning an icon representing a device depicted on the display relative to a depiction of the tissue to indicate the position of the device within the body; and
    monitoring the information received from the first and second sensing systems to evaluate the condition of the tissue over time.

2. A method of monitoring the condition of a tissue comprising:
    implanting a device within a body in proximity to a tissue to be monitored, wherein the device includes the first sensing system and a second sensing system, wherein the first and second sensing systems are configured to sense a physiological property of tissue;
    orienting the device such that the first sensing system senses the physiological property of a first region of a tissue, and the second sensing system senses the same physiological property from a second region of a tissue;
    displaying the orientation of the device relative to the first and the second region of the tissue on a display; and
    positioning an icon representing a device depicted on the display relative to a depiction of the tissue to indicate the position of the device within the body.

3. A method of monitoring the condition of a tissue comprising:
    implanting a device within a body in proximity to tissue to be monitored, wherein the device includes the first sensing system and a second sensing system, wherein the first and second sensing systems are configured to sense a physiological property of tissue;
    orienting the device such that the first sensing system senses the physiological property of a first tissue, and the second sensing system senses the same physiological property from a second tissue;

displaying the orientation of the device relative to the first and the second tissue on a display; and positioning an icon representing the device depicted on the display relative to a depiction of the tissue to indicate the position of the device within the body.

4. A system for monitoring tissue condition comprising:

a housing configured to be implanted between a first tissue and a different second tissue within a patient's body, the housing including a first surface located on a first outer side of the housing configured to rest against the first tissue, and a second surface located on a second outer side of the housing, opposite from the first outer side, configured to rest against the second tissue;

a first sensing system proximate to the first surface configured to sense a physiological property-of the first tissue;

a second sensing system proximate to the second surface configured to sense the same physiological property of the second tissue; and a processing system in communication with the first and second sensing systems configured to compute a difference between the physiological property oxygenation sensed by the first and second sensing systems;

a display configured to depict information about the physiological property sensed by the first or second sensing systems, and to depict an icon representing the device on the display relative to a depiction of the tissue to indicate the position of the device within the body.

5. The method of claim 1, wherein the physiological property is oxygenation and wherein the condition of the first tissue is determined to be normal:

if the oxygenation sensed by the first sensing system is normal.

6. The method of claim 1, wherein the physiological property is oxygenation and wherein the condition of the first tissue is determined to be abnormal:

If the sensed oxygenation sensed by the first sensing system is abnormally low and the oxygenation sensed by the second sensing system is normal.

7. The method of claim 1, wherein the physiological property is oxygenation and wherein the condition of the first tissue is not determined to be abnormal:

if the oxygenation sensed by the first and the second sensing system are abnormally low.

8. A method for determining the condition of a transplanted tissue within a patient's body relative to the condition of surrounding tissue comprising:

implanting a sensing device within the patient's body in proximity to a transplanted tissue and a different native tissue, wherein the device includes the first sensing system and a second sensing system;

orienting the device such that the first sensing system senses the oxygenation of the transplanted tissue, and the second sensing system senses the oxygenation of the native tissue;

comparing the sensed oxygenations by the first and the second sensing systems; and determining whether the condition of the transplanted tissue is normal based on the comparison.

9. The method of claim 8, wherein the condition of the transplanted tissue is determined to be normal:

if the sensed oxygenation of the transplanted tissue is normal.

10. The method of claim 8, wherein the condition of the transplanted tissue is determined to be abnormal:

if the sensed oxygenation of the transplanted tissue is abnormally low and the sensed oxygenation of the second tissue is normal.

11. The method of claim 8, wherein the condition of the transplanted tissue is not determined to be abnormal:

if the sensed oxygenation by the first and the second sensing system are abnormally low.

* * * * *